United States Patent
Liu et al.

(10) Patent No.: US 10,502,544 B2
(45) Date of Patent: Dec. 10, 2019

(54) EFFICIENT SAMPLING OF OPTICAL COHERENCE TOMOGRAPHY DATA FOR EXPLICIT RANGING OVER EXTENDED DEPTH

(71) Applicants: Carl Zeiss Meditec, Inc., Dublin, CA (US); Carl Zeiss Meditec AG, Jena (DE)

(72) Inventors: Yuan Liu, Dublin, CA (US); Nathan Shemonski, San Mateo, CA (US); Matthew J. Everett, Livermore, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 16/308,800

(22) PCT Filed: Jun. 14, 2017

(86) PCT No.: PCT/EP2017/064580
§ 371 (c)(1),
(2) Date: Dec. 10, 2018

(87) PCT Pub. No.: WO2017/216242
PCT Pub. Date: Dec. 21, 2017

(65) Prior Publication Data
US 2019/0145754 A1    May 16, 2019

Related U.S. Application Data

(60) Provisional application No. 62/350,603, filed on Jun. 15, 2016.

(51) Int. Cl.
*G01B 9/02* (2006.01)
*A61B 3/10* (2006.01)

(52) U.S. Cl.
CPC ..... *G01B 9/02009* (2013.01); *G01B 9/02078* (2013.01); *G01B 9/02087* (2013.01); *A61B 3/102* (2013.01); *G01B 9/02091* (2013.01)

(58) Field of Classification Search
CPC ............ G01B 9/02091; G01B 9/02002; G01B 9/02007; G01B 9/02009; G01B 9/02087
See application file for complete search history.

(56) References Cited

U.S. PATENT DOCUMENTS

| | | |
|---|---|---|
| 5,321,501 A | 6/1994 | Swanson et al. |
| 6,002,480 A | 12/1999 | Izatt et al. |

(Continued)

FOREIGN PATENT DOCUMENTS

| | | |
|---|---|---|
| EP | 1770352 A1 | 4/2007 |
| EP | 1870028 A1 | 12/2007 |

(Continued)

OTHER PUBLICATIONS

Akos et al., "Direct Bandpass Sampling of Multiple Distinct RF Signals", IEEE Transactions on Communications, vol. 47, No. 7, Jul. 1999, pp. 983-988.

(Continued)

*Primary Examiner* — Jonathan M Hansen
(74) *Attorney, Agent, or Firm* — Morrison & Foerster LLP

(57) ABSTRACT

An efficient OCT data collection and processing method for obtaining a high-axial-resolution image with explicit ranging over an extended depth is described. The method includes collecting a first dataset at a transverse location of the sample. The first dataset comprises spectra of a bandwidth ($\Delta k_1$) sampled at a spectral sampling interval ($dk_1$). A second dataset comprising spectra of a bandwidth ($\Delta k_2$) sampled at a spectral sampling interval ($dk_2$) is collected. The bandwidth $\Delta k_2$ is less than $\Delta k_1$ and spectral sampling (Continued)

interval $dk_2$ is less than $dk_1$. The first and the second datasets are processed to generate at least one A-scan with an axial resolution higher than the axial resolution corresponding to the bandwidth $\Delta k_2$ and a depth range larger than the depth range provided by sampling interval $dk_1$.

21 Claims, 8 Drawing Sheets

(56) References Cited

U.S. PATENT DOCUMENTS

| | | | |
|---|---|---|---|
| 6,769,769 | B2 | 8/2004 | Podoleanu et al. |
| 7,019,838 | B2 | 3/2006 | Izatt et al. |
| 7,330,270 | B2 | 2/2008 | O'Hara et al. |
| 7,336,366 | B2 | 2/2008 | Choma et al. |
| 7,359,062 | B2 | 4/2008 | Chen et al. |
| 7,391,520 | B2 | 6/2008 | Zhou et al. |
| 7,480,058 | B2 | 1/2009 | Zhao et al. |
| 7,602,500 | B2 | 10/2009 | Izatt et al. |
| 7,630,083 | B2 | 12/2009 | De Boer et al. |
| 7,742,174 | B2 | 6/2010 | Izatt et al. |
| 7,872,757 | B2 | 1/2011 | De Boer et al. |
| 7,929,146 | B2 | 4/2011 | Izatt et al. |
| 7,990,541 | B2 | 8/2011 | Izatt et al. |
| 8,054,468 | B2 | 11/2011 | De Boer et al. |
| 8,180,131 | B2 | 5/2012 | Toth et al. |
| 8,348,427 | B2 | 1/2013 | Buckland et al. |
| 8,529,062 | B2 | 9/2013 | Buckland et al. |
| 8,570,525 | B2 | 10/2013 | Wojdas et al. |
| 8,757,803 | B2 | 6/2014 | Everett et al. |
| 8,770,755 | B2 | 7/2014 | Buckland et al. |
| 8,860,948 | B2 | 10/2014 | Abdulhalim et al. |
| 8,937,724 | B2 | 1/2015 | Vakoc et al. |
| 9,014,451 | B2 | 4/2015 | Beg et al. |
| 9,163,930 | B2 | 10/2015 | Buckland et al. |
| 9,192,294 | B2 | 11/2015 | Sharma et al. |
| 9,259,150 | B2 | 2/2016 | Izatt et al. |
| 9,279,659 | B2 | 3/2016 | Izatt et al. |
| 9,348,195 | B2 | 5/2016 | Kwon et al. |
| 9,433,353 | B2 | 9/2016 | Hanebuchi |
| 9,441,948 | B2 | 9/2016 | Vakoc et al. |
| 9,709,379 | B2 * | 7/2017 | Kemp .............. G01B 9/02004 |
| 2007/0076220 | A1 | 4/2007 | Kawahara |
| 2013/0271772 | A1 * | 10/2013 | Johnson ............ G01B 9/02004 356/479 |
| 2016/0157721 | A1 | 6/2016 | Vakoc et al. |
| 2018/0209778 | A1 * | 7/2018 | Al-Qaisi ............ G01B 9/02069 |

FOREIGN PATENT DOCUMENTS

| EP | 1870029 A1 | 12/2007 |
|---|---|---|
| EP | 1870030 A1 | 12/2007 |
| EP | 1770352 B1 | 7/2008 |

OTHER PUBLICATIONS

Amano et al., "Optical Frequency-Domain Reflectometry with a Rapid Wavelength-Scanning Superstructure-Grating Distributed Bragg Reflector Laser", Applied Optics, vol. 44, No. 5, Feb. 10, 2005, pp. 808-816.
Bajraszewski et al., "Improved Spectral Optical Coherence Tomography using Optical Frequency Comb", Optics Express, vol. 16, No. 6, Mar. 17, 2008, pp. 4163-4176.
Baumann et al., "Full Range Complex Spectral Domain Optical Coherence Tomography Without Additional Phase Shifters", Optics Express, vol. 15, No. 20, Oct. 1, 2007, pp. 13375-13387.
Choma et al., "Instantaneous Quadrature Low-Coherence Interferometry with 3 X 3 Fiber-Optic Couplers", Optics Letters, vol. 28, No. 22, Nov. 15, 2003, pp. 2162-2164.
Coulson et al., "Frequency-Shifting using Bandpass Sampling", IEEE Transactions on Signal Processing, vol. 42, No. 6, Jun. 1994, pp. 1556-1559.

Dhalla et al., "Complete Complex Conjugate Resolved Heterodyne Swept-Source Optical Coherence Tomography using a Dispersive Optical Delay Line", Biomedical Optics Express, vol. 2, No. 5, May 1, 2011, pp. 1218-1232.
Dsouza et al., "Dermascope Guided Multiple Reference Optical Coherence Tomography", Biomedical Optics Express, vol. 5, No. 9, Sep. 1, 2014, pp. 2870-2882.
Goldberg et al., "Performance of Reduced Bit-Depth Acquisition for Optical Frequency Domain Imaging", Optics Express, vol. 17, No. 19, Sep. 14, 2009, pp. 16957-16968.
Groot et al., "Three-Dimensional Imaging by Sub-Nyquist Sampling of White-Light Interferograms", Optics Letter, vol. 18, No. 17, Sep. 1, 1993, pp. 1462-1464.
Hofer et al., "Dispersion Encoded Full Range Frequency Domain Optical Coherence Tomography", Optics Express, vol. 17, No. 1, Jan. 5, 2009, pp. 7-24.
International Preliminary Report on Patentability received for PCT Patent Application No. PCT/EP2017/064580, dated Dec. 27, 2018, 9 pages.
International Search Report and Written Opinion received for PCT Application No. PCT/EP2017/064580, dated Sep. 1, 2017, 10 pages.
Jung et al., "Spectrally-Sampled OCT for Sensitivity Improvement from Limited Optical Power", Optics Express, vol. 16, No. 22, Oct. 27, 2008, pp. 17457-17467.
Lee et al., "Optimization for Axial Resolution, Depth Range, and Sensitivity of Spectral Domain Optical Coherence Tomography at 1.3 µm", Journal of the Korean Physical Society, vol. 55, No. 6, Dec. 2009, pp. 2354-2360.
Leitgeb et al., "Complex Ambiguity-Free Fourier Domain Optical Coherence Tomography through Transverse Scanning", Optics Letters, vol. 32, No. 23, Dec. 1, 2007, pp. 3453-3455.
Motaghian Nezam et al., "Increased Ranging Depth in Optical Frequency Domain Imaging by Frequency Encoding", Optics Letters, vol. 32, No. 19, Oct. 1, 2007, pp. 2768-2770.
Podoleanu et al., "Simultaneous En-Face Imaging of Two Layers in the Human Retina by Low-Coherence Reflectometry", Optics Letters, vol. 22, No. 13, Jul. 1, 1997, pp. 1039-1041.
Siddiqui et al., "Optical-Domain Subsampling for Data Efficient Depth Ranging in Fourier-Domain Optical Coherence Tomography", Optics Express, vol. 20, No. 16, Jul. 30, 2012, pp. 17938-17951.
Siddiqui, Meena, "Optical Domain Subsampling for Data-Efficient Optical Coherence Tomography (OCT)", Massachusetts Institute of Technology (MIT), 2013, pp. 1-100.
Tozburun et al., "A Rapid, Dispersion-based Wavelength-Stepped and Wavelength-Swept Laser for Optical Coherence Tomography", Optics Express, vol. 22, No. 3, Feb. 10, 2014, pp. 3414-3424.
Tsai et al., "Frequency Comb Swept Lasers", Optics Express, vol. 17, No. 23, Nov. 9, 2009, pp. 21257-21270.
Vakoc et al., "Elimination of Depth Degeneracy in Optical Frequency-Domain Imaging Through Polarization based Optical Demodulation", Optics Letters, vol. 31, No. 3, Feb. 1, 2006, pp. 362-364.
Vaughan et al., "The Theory of Bandpass Sampling", IEEE Transactions on Signal Processing, vol. 39, No. 9, Sep. 1991, pp. 1973-1984.
Wojtkowski et al., "Full Range Complex Spectral Optical Coherence Tomography Technique in Eye Imaging", Optics Letters, vol. 27, No. 16, Aug. 15, 2002, pp. 1415-1417.
Yun et al., "Removing the Depth-Degeneracy in Optical Frequency Domain Imaging with Frequency Shifting", Optics Express, vol. 12, No. 20, Oct. 4, 2004, pp. 4822-4828.
Zhang et al., "Removal of a Mirror Image and Enhancement of the Signal-to-Noise Ratio in Fourier-Domain Optical Coherence Tomography using an Electro-Optic Phase Modulator", Optics Letters, vol. 30, No. 2, Jan. 15, 2005, pp. 147-149.
Zurauskas et al., "Simultaneous Multiple-Depths En-Face Optical Coherence Tomography using Multiple Signal Excitation of Acousto-Optic Deflectors", Optics Express, vol. 21, No. 2, Jan. 28, 2013, pp. 1925-1936.

* cited by examiner (Prior-art)

EFFICIENT SAMPLING OF OPTICAL COHERENCE TOMOGRAPHY DATA FOR EXPLICIT RANGING OVER EXTENDED DEPTH

PRIORITY

The present application is a National Phase application under 35 U.S.C. § 371 of International Application No. PCT/EP2017/064580, filed Jun. 14, 2017, which claims priority to U.S. Provisional Application Ser. No. 62/350,603, filed on Jun. 15, 2016, the contents of each of which are hereby incorporated by reference in their entirety.

TECHNICAL FIELD OF THE INVENTION

This invention relates to the field of sampling of optical coherence tomography (OCT) data. In particular, the invention discloses a method for efficient sampling of OCT data for explicit ranging over an extended depth range.

BACKGROUND

Optical Coherence Tomography (OCT) is an interferometric technique for performing high-resolution cross-sectional imaging that can provide images of samples including tissue structure on the micron scale in situ and in real time. OCDR is the one-dimensional analog of OCT. OCT is based on the principle of low coherence interferometry (LCI) and determines the scattering profile of a sample along the OCT beam by detecting the interference of light reflected or scattered from a sample and a reference beam. Each scattering profile in the depth direction (z) is called an axial scan, or A-scan. Cross-sectional images (B-scans), and by extension 3D volumes, are built up from many A-scans, with the OCT beam moved to a set of transverse (x and y) locations on the sample. OCT can be categorized into time-domain OCT (TD-OCT) and Fourier-domain OCT (FD-OCT). In time domain OCT (TD-OCT), the path length difference between light returning from the sample and reference light is translated longitudinally in time to recover the depth information in the sample. In frequency-domain or Fourier-domain OCT (FD-OCT), a method based on diffraction tomography, the broadband interference between reflected sample light and reference light is acquired in the frequency domain and a Fourier transform is used to recover the depth information. The sensitivity advantage of FD-OCT over TD-OCT is well established.

There are two common approaches to FD-OCT. One is spectral-domain OCT (SD-OCT) where the interfering light is spectrally dispersed prior to detection and the full depth information at a single transverse location on the sample can be recovered from a single exposure. The second is swept-source OCT (SS-OCT) where the source is swept over a range of optical frequencies and detected in time, therefore encoding the spectral information in time. In traditional point scanning or flying spot techniques, a single point of light is scanned across the sample. In parallel techniques, a series of spots (multi-beam), a line of light (line-field), or a two-dimensional field of light (partial-field and full-field) is directed to the sample. The resulting reflected light is combined with reference light and detected. Parallel techniques can be accomplished in TD-OCT, SD-OCT or SS-OCT configurations. OCT techniques have found great use in the field of ophthalmology.

In FD-OCT, the depth range over which an image is taken is inversely proportional to the spectral sampling interval of the spectral interferogram recorded by the system. Denser or finer sampling (more samples per wavenumber) enables longer depth range without aliasing as given by Nyquist sampling criterion (see for example, Lee et al., "Optimization for axial resolution, depth range, and sensitivity of spectral domain optical coherence tomography at 1.3 µm," Journal of the Korean Physical Society, 2009). The spectral resolution (i.e., the smallest difference in wavelengths or wavenumbers that two spectral samples can be distinguished) is also an important factor in imaging over a certain depth range because it determines the depth-dependent sensitivity roll-off. If the spectral resolution is sufficiently high, then the signal beyond the depth range (i.e., signal over extended depth range) could be aliased into and collected in the depth range. Advances in light sources and detection systems have enabled higher spectral resolution and therefore imaging over extended depth range. Various embodiments of higher spectral resolution FD-OCT for extended depth range have been proposed and experimentally demonstrated in the past (see for example, U.S. Pat. Nos. 7,990,541; 9,163,930; EP 1,870,028; Jung et al., "Spectrally-sampled OCT for sensitivity improvement from limited optical power," Optics Express, 2008; Tsai et al., "Frequency comb swept lasers," Optics Express, 2009). While long depth range may be preferable in certain applications, for example wide-field retinal imaging, the high spectral resolution demands a large sampling number for full-depth high-axial-resolution imaging under the Nyquist sampling criterion. The large sampling number or data size can lower the acquisition and the processing speed, increase the system requirements, and present a memory burden.

Subsampling of FD-OCT data has been demonstrated as a compressive sensing method in extended depth imaging (see for example, U.S. Pat. No. 8,937,724; Siddiqui et al., "Optical-domain subsampling for data efficient depth ranging in Fourier-domain optical coherence tomography," Optics Express, 2012). Subsampling is a well-known technique in telecommunication to down-convert the high-frequency signals to a lower-frequency baseband. In FD-OCT, subsampling aliases the high-frequency fringes to low-frequency ones and thus the image at the extended depth range is wrapped into the baseband depth window set by the sampling rate. In the prior works, quadrature detection was employed to detect the complex-valued interferogram which could avoid non-circular wrapping of extended depth signals, and the samples of limited depth extents were imaged without overlap in the baseband window. By concatenating copies of the baseband image, the actual image was assembled spanning an extended depth range, but many undesired duplicates of the image prevented a clear interpretation of the data. A surface finding procedure was suggested to recover the actual image, but the explicit depth ranging, which is localization of the true optical delay relative to the reference depth location, is undetermined from such a procedure. In addition, surface-finding procedures could work well for continuous structures such as the human retina, but will fail for non-continuous structures such as when imaging a surgical tool many millimeters above the surface of the tissue. Thus, there is a need for a method, a process, and/or an approach to efficiently collect and process the FD-OCT data for explicit ranging over extended depth.

SUMMARY

An efficient data collection and processing method is described for obtaining high-axial-resolution data with explicit depth ranging using an OCT system. The method makes use of at least two sampling techniques in which one of the sampling techniques involves sampling a broad bandwidth at a wide spectral sampling interval to collect at least a first OCT dataset for obtaining a high-axial-resolution image in which the extended depth signals are aliased to the baseband window. The other sampling technique involves sampling the same location or set of locations with a narrower bandwidth at a reduced spectral sampling interval (i.e., more samples per wavenumber) to collect at least a second OCT dataset for obtaining a low-axial-resolution image spanning an extended depth range relative to the first OCT dataset. The method involves processing the aforementioned OCT datasets to generate at least one A-Scan having an axial resolution greater than the axial resolution corresponding to the bandwidth of the second OCT dataset and a depth range greater than depth range provided by the sampling interval of the first dataset. The processing allows detection of the true depth window to generate an OCT dataset of an extended depth range and high axial resolution. In one embodiment, the processing may include, without limitation, Fourier transforming, filtering, multiplying, and generating binary masks from the OCT datasets.

The method discussed herein is advantageous in a number of respects. For instance, the method allows unambiguous determination of the depth location of the imaging signal wrapped in the baseband, thus enabling high-axial-resolution imaging with explicit depth ranging in addition to the reduced sample size.

It should be noted that the features and/or advantages described herein are not all-inclusive and many additional features and/or advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 3A shows conventional Nyquist sampling (e.g., full sampling bandwidth with narrow spectral sampling intervals). FIG. 3B shows broadband sparse sampling (e.g., broad or full sampling bandwidth with wide spectral sampling intervals). FIG. 3C shows narrowband dense sampling (e.g., narrow sampling bandwidth with reduced or narrow spectral sampling intervals). FIGS. 3D and 3E show other examples of broadband sparse sampling and narrowband dense sampling, respectively, for rectangular shaped pulses. The definitions of the sampling parameters are also displayed in FIG. 3A: spectral resolution $\delta k$, spectral sampling interval $dk$, and bandwidth $\Delta k$.

FIG. 4A shows the B-scan and its spectra of the corresponding A-scans under conventional Nyquist sampling. FIG. 4B shows those of the broadband sparse sampling. FIG. 4C shows those of the narrowband dense sampling. The dimensions of the B-scans are 3 mm (transverse)×2 mm (axial).

FIG. 8A shows the final output image using the true imaging depth window detected based on a first detection approach (maximum-signal approach). FIG. 8B shows the final output image using the true imaging depth window detected based on a second detection approach (center-of-mass approach). FIG. 8C shows another example of producing the final output image using the true imaging depth window detected based on the maximum-signal approach. FIG. 8D shows another example of producing the final output image using the true imaging depth window detected based on the center-of-mass approach.

FIG. 10 illustrates efficient sampling of FD-OCT data of a human eye with varying numbers of sampling points in broadband sparse sampling. In particular.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirely.

Example Optical Coherence Tomography (OCT) System

Figure 1:
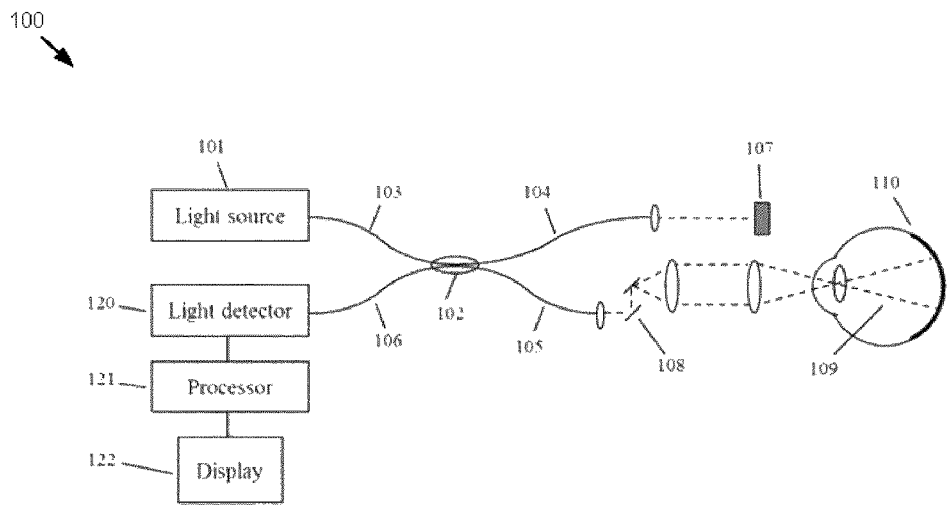
FIG. 1 illustrates a generalized optical coherence tomography (OCT) system that can be used to practice the present invention.

A generalized FD-OCT system 100 used to collect three-dimensional image data suitable for use with the present invention is illustrated in FIG. 1. A FD-OCT system 100 includes a light source 101, typical sources including but not limited to a broadband light source with short temporal coherence length in the case of SD-OCT or a wavelength tunable laser source in the case of SS-OCT. A beam of light from source 101 is routed, typically by optical fiber 103 and 105, to illuminate the sample 110, a typical sample being tissues in the human eye. The light can be scanned, typically with a scanner 108 between the fiber output and the sample, so that the beam of light (dashed line 109) is scanned laterally (in x and/or y) over the region of the sample to be imaged. Light scattered from the sample is collected, typically into the same fiber 105 used to route the light for illumination. Reference light derived from the same source 101 travels a separate path, in this case involving fiber 104 and retro-reflector 107 with an adjustable optical delay. Those skilled in the art recognize that a transmissive reference path could also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers could be used for balanced or unbalanced detection of the interference signal. The output from the detector 120 is supplied to a processor 121 that converts the observed interference signals into depth information of the sample. The results could be stored in the processor 121 or other storage medium or displayed on display 122. The sample and reference arms in the interferometer could consist of bulk-optics, fiber-optics or hybrid bulk-and-fiber-optics systems and could have different architectures such as Michelson, Mach-Zehnder or common-path based designs as would be known by those skilled in the art. Light beam as used herein should be interpreted as any carefully directed light path. Spectrometers are typically used at the detection port for SD-OCT systems, while balanced detectors are typically used in SS-OCT systems.

The interference causes the intensity of the interfered light to vary across the spectrum. The Fourier transform of the interference signal reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (B-scan or tomogram) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern. The efficient sampling and processing techniques described herein can be applied to a single A-scan (OCDR) without scanning the beam across a range of transverse locations or to multiple A-scans from a plurality of transverse locations on the sample.

In some embodiments, the FD-OCT system may employ a quadrature detection apparatus. Quadrature detection of the interference prevents non-circular wrapping of extended depth signals and the resulting signal overlap that can not be clearly distinguished through post-processing. It should be recognized by those skilled in the art that quadrature detection could be implemented using a number of methods reported in the prior art, with corresponding modifications to a general FD-OCT system such as that shown in FIG. 1. For instance, in the phase shifting method (see for example, U.S. Pat. No. 7,929,146; Wojtkowski et al., "Full range complex spectral optical coherence tomography technique in eye imaging," Optics Letter, 2002), a phase shifting device could be introduced into the system (e.g., a piezo motor to translate the retro reflector 107) to acquire phase-shifted interferograms for obtaining the complex-valued signal. Other quadrature detection methods include, but are not limited to, 3×3 fiber coupling (see for example, U.S. Pat. No. 7,019,838; Choma et al., "Instantaneous quadrature low-coherence interferometry with 3×3 fiber-optic couplers," Optics Letter, 2003), frequency shifting (see for example, U.S. Pat. No. 9,279,659; Yun et al., "Removing the depth-degeneracy in optical frequency domain imaging with frequency shifting," Optics Express, 2004), polarization demodulation, (see for example, U.S. Pat. No. 9,441,948; Vakoc et al., "Elimination of depth degeneracy in optical frequency-domain imaging through polarization-based optical demodulation," Optics Letter, 2006), B-scan phase shift (see for example, Leitgeb et al., "Complex ambiguity-free Fourier domain optical coherence tomography through transverse scanning," Optics Letter, 2007), and dispersion encoded algorithm (see for example, U.S. Pat. No. 7,330,270; Hofer et al., "Dispersion encoded full range frequency domain optical coherence tomography," Optics Express, 2008).

It should be recognized that the invention described herein could be applied to different variations of SD-OCT and SS-OCT systems. For SD-OCT, more than one broadband spectrally continuous or discrete light sources 101 could be used. For example, one source could provide the broad bandwidth, sparsely sampled data and the other source could provide the narrow bandwidth, densely sampled data. The sources need not have the same spectral ranges. To assist in the collection of at least one broadband sparsely sampled dataset and at least one narrowband densely sampled dataset, the light beams could be changed or modulated by inserting at least one optical element (e.g., bandpass filter or periodic filter) in the source 101, the sample 110, the reference 104, and/or the detection 106 arms to produce the desired spectra (see for example, U.S. Pat. Nos. 8,937,724 and 8,757,803). The detection apparatus 120 may consist of more than one parallel detector (e.g., a spectrometer) that allows parallel or sequential acquisition of the data. The detectors need not have the same spectral resolution and the spectral sampling interval. Although quadrature detection may help in distinguishing image overlap due to aliasing, the approaches described herein could also be used without quadrature detection.

For SS-OCT, more than one swept-wavelength or stepped-wavelength light source 101 could be used. The sources need not have the same spectral range, spectral resolution, and sweep rate or wavelength step. The wavelength scanning of the light sources could be in parallel or sequential. The light beams could be changed or modulated by inserting at least one optical element in the source 101, the sample 110, the reference 104, and the detection 106 arms. The detection apparatus 120 may consist of more than one detectors that allow parallel or sequential acquisition of the data. In addition, a combined FD-OCT system, including more than one SD-OCT subsystem and more than one SS-OCT subsystem, may provide the same desired functionalities.

The processing and storing functions may be localized within the OCT instrument or functions may be performed on an external processing unit (e.g., a computer system) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

Example Method

Figure 2A:
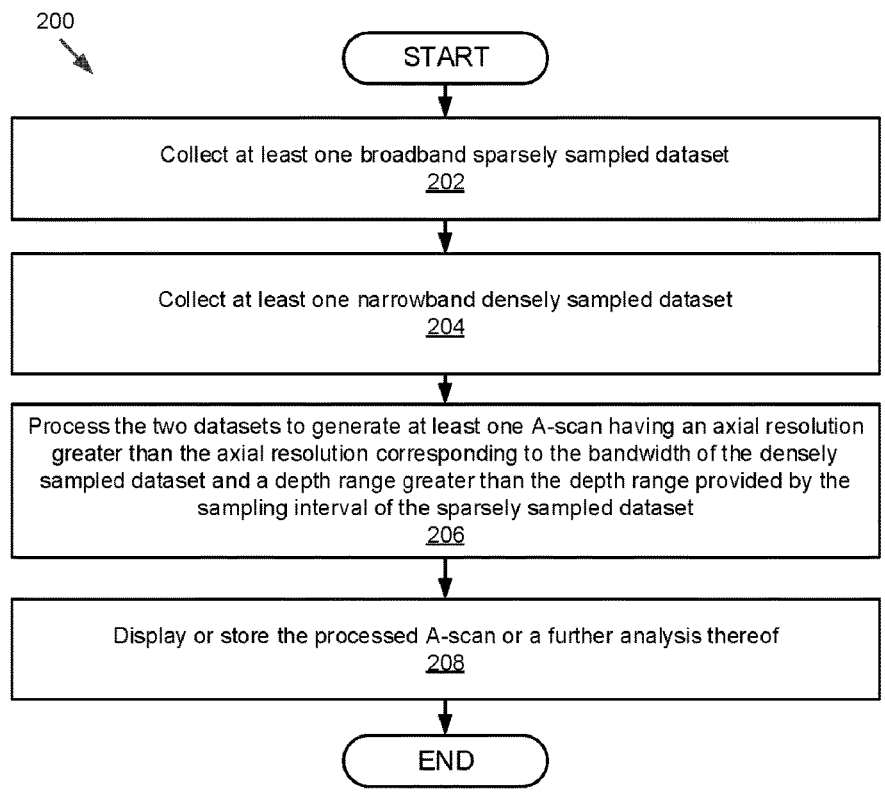
FIG. 2a is a flowchart of a general method for efficient collecting and processing of OCT data for explicit ranging over an extended depth.

A general method 200 for efficiently collecting and processing OCT data for explicit ranging (e.g., localization of the true optical delay relative to the reference depth location) over an extended depth is illustrated in FIG. 2a. It should be understood that the method 200 described herein is not limited to the steps and/or operations referenced in this method and that other steps and/or operations are also possible and are within the scope of the present disclosure. It should also be understood that not every step described herein must be performed, order of the steps may be changed, and/or additional steps may be added for different applications.

Figure 3A:
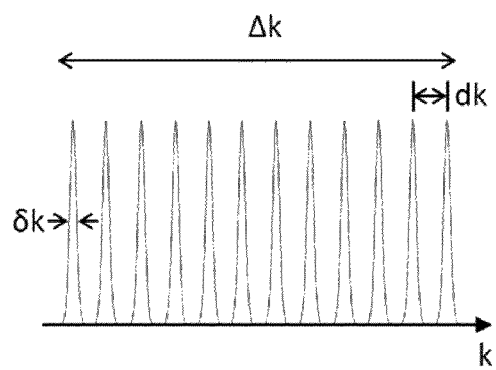
FIGS. 3A-3E are schematic illustrations of sampling of FD-OCT data. In particular.

For the purposes of better describing and/or understanding steps 202 and 204 of method 200 a conventional Nyquist sampling is shown in FIG. 3A. A full or broad bandwidth ($\Delta k$) is sampled at a narrow spectral sampling interval (dk) (i.e., sampled at twice the highest frequency of the interference signal). Here, ($\delta k$) indicates the spectral resolution. It should be understood that the Nyquist sampling shown in FIG. 3A is only for understanding purposes and is not part of the sampling process discussed in method 200.

Figure 3B:
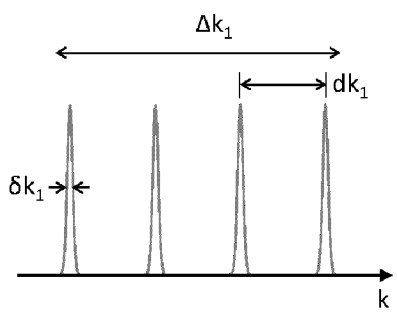
Figure 3D:
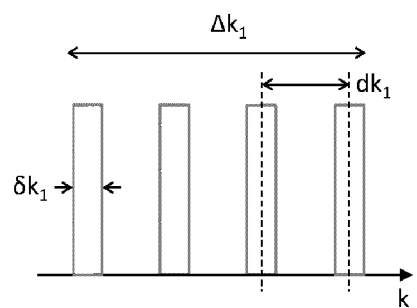

The method 200 begins by collecting, in block 202, at least one broadband sparsely sampled dataset, which comprises spectra of a bandwidth ($\Delta k_1$) sampled at a spectral sampling interval ($dk_1$) (see FIG. 3B). A prior subsampling scheme may be used to collect said dataset (see for example, U.S. Pat. No. 8,937,724). In some embodiments, the dataset is collected using the FD-OCT of FIG. 1 by scanning a transverse location or set of transverse locations on a sample (e.g., the sample 110) in a first mode with a certain spectral range, spectral resolution, and spectral sampling interval. In one embodiment, the broadband sparsely sampled dataset (202) is collected based on a sampling shown in FIG. 3B. In another embodiment, the dataset may be collected based on a sampling shown in FIG. 3D where the shape of the spectral sample (302) is a rect function and the spectral resolution ($\delta k_1$) is equal to the spectral sampling interval ($dk_1$). In some instances, the dataset may be Fourier-transformed to generate a high-axial-resolution image in which the signals over the extended depth range are aliased into the reduced baseband image, such as the baseband image 408 shown in FIG. 4B (discussed in further details below). An object of interest is captured, but the reconstruction of the image over an extended depth range is undetermined, which can be resolved using a narrowband dense sampling as discussed with respect to block 204 below.

Figure 3C:
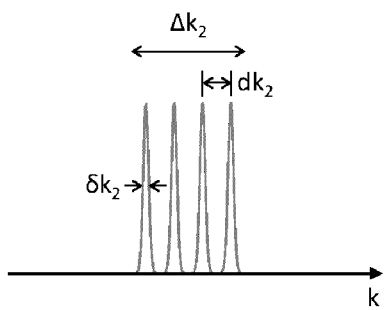
Figure 3E:
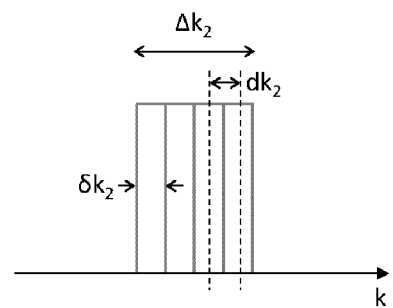

In block 204, at least one narrowband densely sampled dataset is collected over the same transverse location(s) or a subset of the transverse locations. The narrowband densely sampled dataset comprises spectra of a narrower bandwidth ($\Delta k_2$) sampled at a denser spectral sampling interval ($dk_2$) (see FIG. 3C) compared to the first dataset, such that $\Delta k_2$ is less than $\Delta k_1$ and $dk_2$ is less than $dk_1$. In some embodiments, the narrowband densely sampled dataset is collected using the FD-OCT of FIG. 1 by scanning a sample (e.g., the sample 110) in a second mode with a certain spectral range, spectral resolution, and spectral sampling interval. In some instances a single A-scan is collected without scanning. In one embodiment, the narrowband densely sampled dataset (204) is collected based on the sampling scheme shown in FIG. 3C. In another embodiment, the dataset may be collected based on the sampling shown in FIG. 3E where the shape of the spectral sample (302) is a rect function and the spectral resolution ($\delta k_2$) is equal to the spectral sampling interval ($dk_2$). In some instances, the spectral resolution and spectral sampling interval may be different. In some instances, the narrowband densely sampled dataset may be Fourier-transformed to generate a low-axial-resolution image, as discussed later below. The high-axial-resolution image from the broadband sparsely sampled dataset (block 202) in combination with the low-axial-resolution image from the narrowband densely sampled dataset (block 204) facilitates the reconstruction of the high-axial-resolution image over the extended depth range with explicit ranging.

Figure 4A:
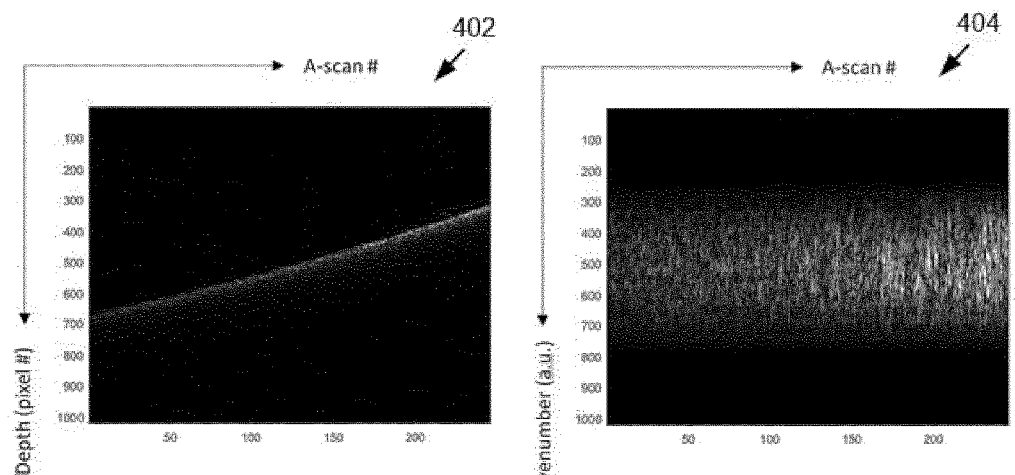
FIGS. 4A-4C illustrate efficient sampling of FD-OCT data of a test eye. In particular.
Figure 4B:
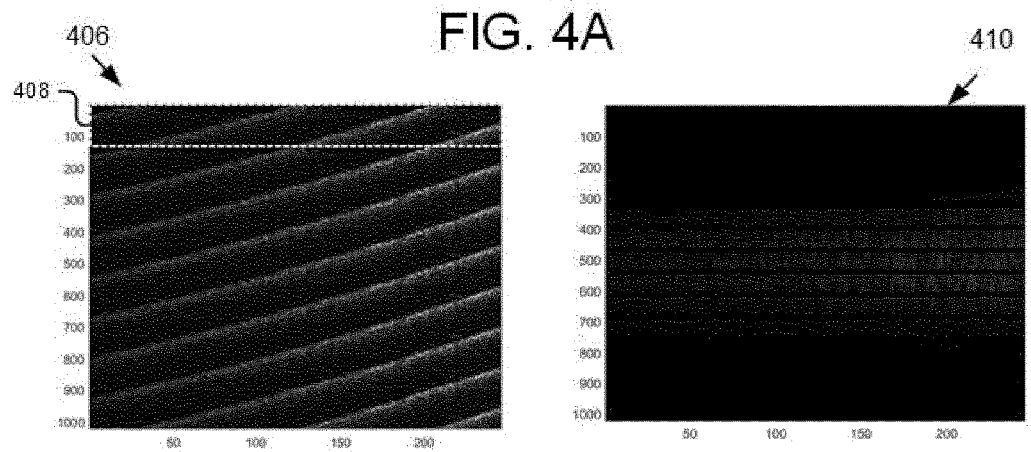
Figure 4C:
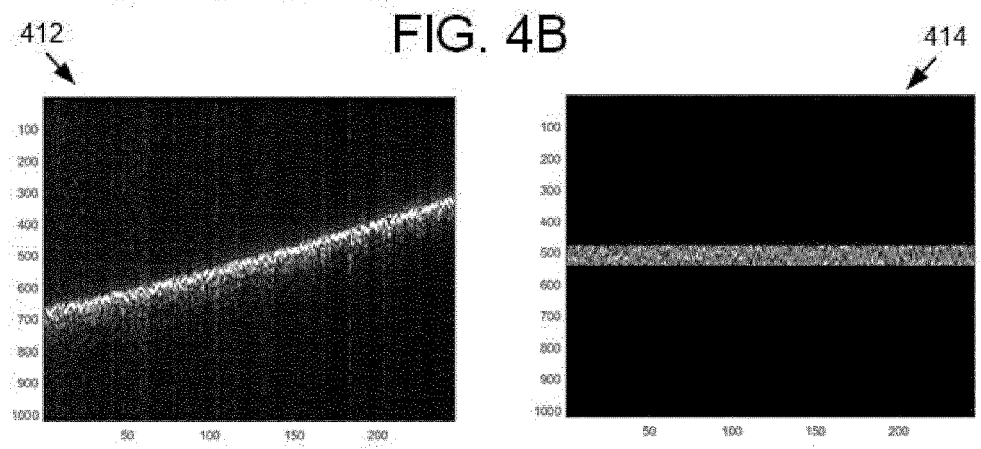

The two sampling approaches discussed above with respect to block 202 (e.g., FIG. 3B) and block 204 (e.g., FIG. 3C) as well as the conventional Nyquist sampling (e.g., FIG. 3A) are further illustrated in FIGS. 4A-4C. FIGS. 4A-4C show B-scans (left) and the interference spectra of the corresponding A-scans (right) of a complex-valued FD-OCT dataset of a test eye based on the three sampling approaches discussed herein. In particular, FIG. 4A shows the B-scan (402) and the interference spectra of the corresponding A-scans (404) of the original dataset of Nyquist sampling. FIG. 4B shows the B-scan (406) and the interference spectra of the corresponding A-scans (410) of the broadband sparse sampling, and FIG. 4C shows the B-scan (412) and the spectra of corresponding A-scans (414) of the narrowband dense sampling. With respect to FIG. 4B, the broadband sparse sampling is performed at a spectral sampling interval which is 8 times that of the Nyquist sampling (i.e., every $8^{th}$ wavenumber as compared to Nyquist sampling). By performing the broadband sampling at 8-times the Nyquist sampling interval, the full-depth-range image is aliased to the baseband image of only ⅛ pixel number, 128, axially, as shown in the dashed box 408. Sampling at this spectral sampling interval (i.e., at 8-times of Nyquist sampling interval) is arbitrary and should be determined by the sample's depth extent so that the aliased signals do not overlap in the baseband image 408. The wavenumbers not sampled in the broadband sparse sampling are then zero-padded to the original sampling number, 1024, of the Nyquist sampling, resulting in 8 duplicate images of the baseband image 408 over the full depth of field with the same SNR. The unfolded images of the sample are present, but the undesired duplicate images prevent a clear interpretation of data. With respect to FIG. 4C, the narrowband dense sampling is performed with a bandwidth which is 1/16 times of that in the conventional Nyquist sampling (i.e., the narrowband dense sampling is done at the center 64 wavenumbers). The wavenumbers outside the spectral range of the narrowband dense sampling are then zero-padded to the original sampling number 1024, resulting in a low-axial-resolution version (412) of the original image (402). This dense sampling number 64 is arbitrary but should be sufficiently large to resolve the depth extent of the sample and to alleviate any speckle effect. In a general case, the broadband sparse sampling number and the narrowband dense sampling number are roughly inversely proportional to each other, depending on the algorithm implementation. The longer the imaging depth window is, the more broadband sparse sampling points are needed to image at high resolution, and the less narrowband dense sampling points with smaller overall bandwidth are needed to locate the depth window. The integrated intensity of A-scans is normalized across the B-scan to account for its variation (414). The resulting low-axial-resolution image (412) shows the true depth location and facilitates the reconstruction of the high-axial-resolution image with explicit depth ranging, as discussed further below.

Figure 8A:
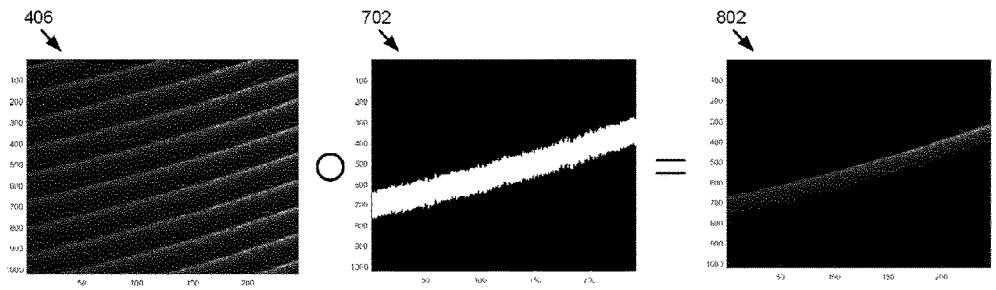
FIGS. 8A-8D each illustrates an example of producing a final output image using the true imaging depth window discussed with respect to FIGS. 7A-7C. In particular.
Figure 8B:
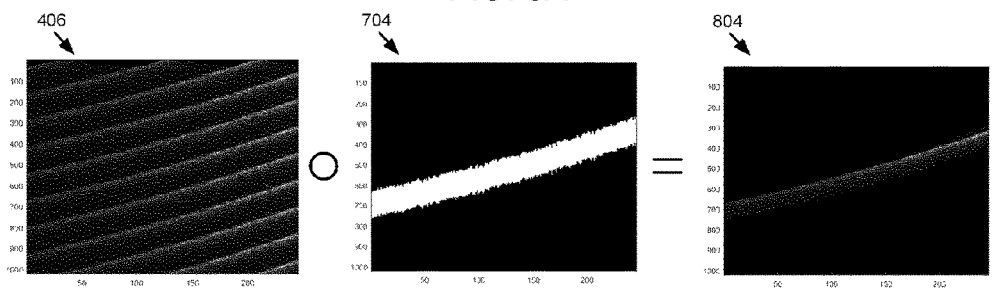
Figure 8C:
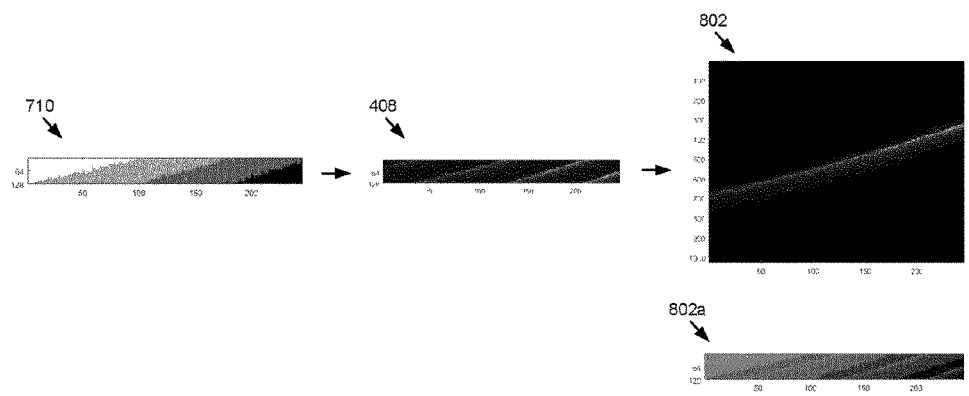
Figure 8D:
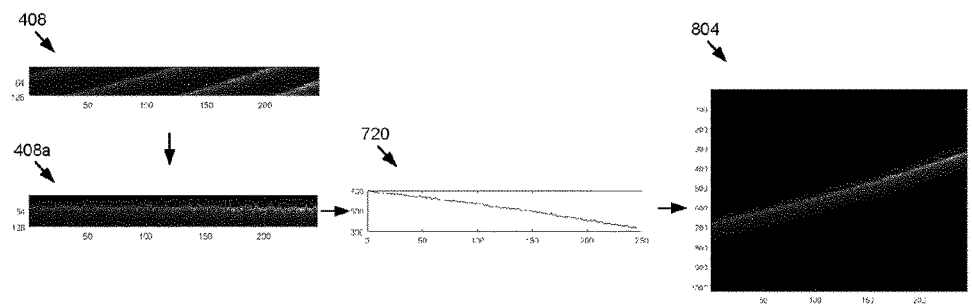

Returning back to method 200, once the broadband sparsely sampled dataset (block 202) and the narrowband densely sampled dataset (block 204) are collected, these datasets are processed to generate at-least one A-scan having an axial resolution greater than the axial resolution corresponding to the bandwidth $\Delta k_2$, and a depth range greater than the scan depth provided by the spectral sampling interval $dk_1$ (step 206). In some embodiments, the processed A-scan can have an axial resolution corresponding to the bandwidth ($\Delta k_1$) (see FIG. 3B). In some embodiments, a plurality of such A-scans may be generated over a set of transverse locations on the sample to form a high-axial-resolution B-scan with an extended depth range, such as for example B-scan 802 (FIG. 8A) or B-scan 804 (FIG. 8B), as discussed in further details below. Once processed the A-scan (or collection of A-scans) can be displayed, stored or further analyzed (block 208).

Figure 2B:
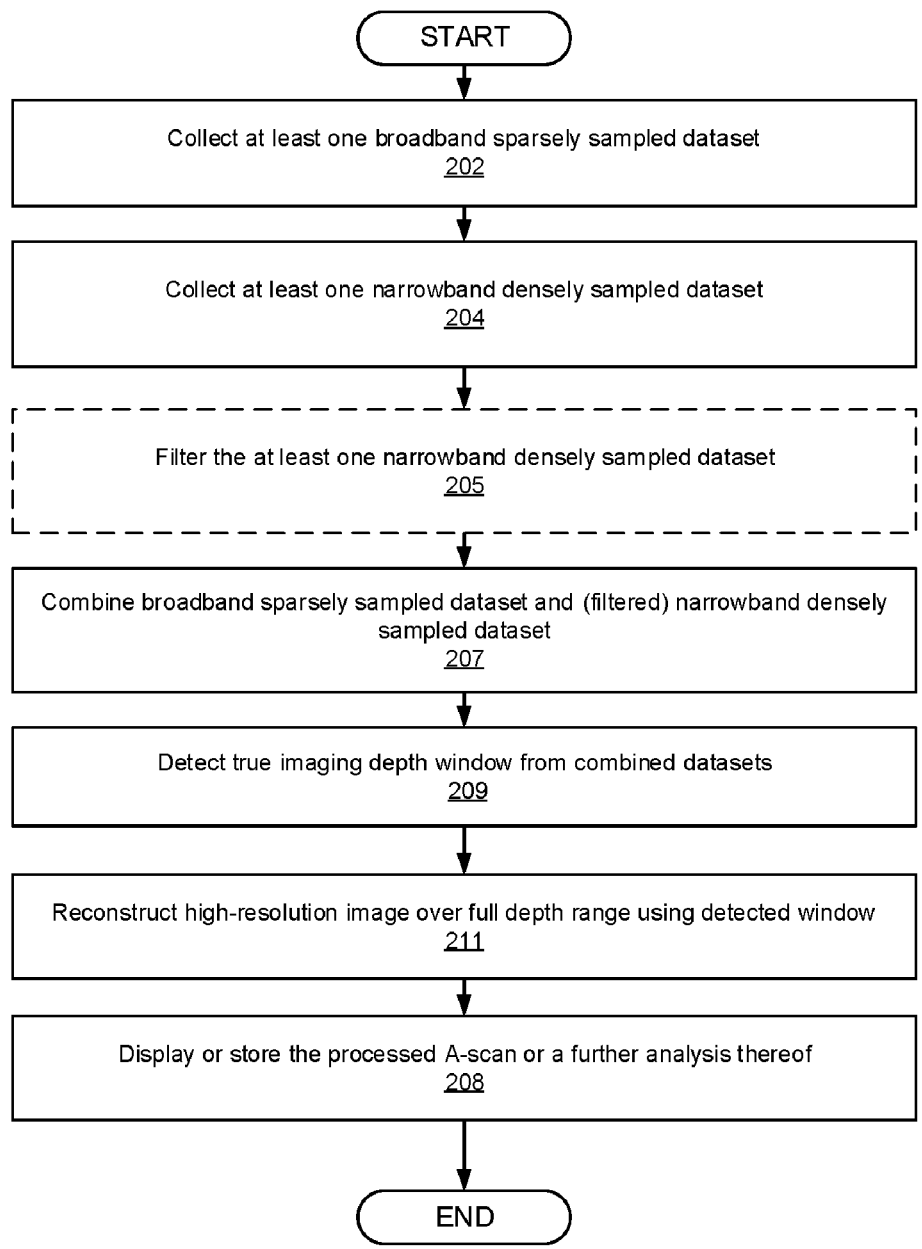
FIG. 2b is a flowchart illustrated one detailed approach to efficient collection and processing of OCT data for explicit ranging over an extended depth range.

FIG. 2b illustrates one particular embodiment. After collecting the two datasets analogous to FIG. 2a, processing block 206 involves a series of steps including, filtering one or more of these datasets (205), combining the datasets (207), detecting a true imaging depth window from the combined or individual datasets (209), and then generating a high-axial-resolution image over an extended depth range using the detected window (211). More details each step are discussed in further details below.

Figure 5:
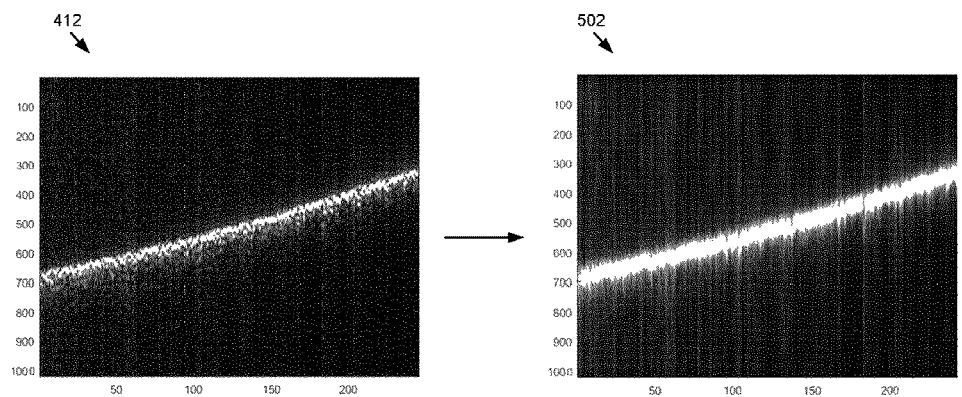
FIG. 5 illustrates an exemplary filtered image obtained upon filtering a narrowband densely sampled image according to one embodiment of the present invention.

In block 205, a one-dimensional Gaussian filtering along the axial direction may optionally be performed on the broadband sparsely sampled or the narrowband densely sampled dataset or both. In a preferred embodiment, the filtering may be performed on the narrowband densely sampled dataset, which is equivalent to multiplying the spectra of A-scans by a Gaussian function. For example, FIG. 5 shows an exemplary filtered image (502) upon filtering the low-axial-resolution image (412). The purpose of the filtering discussed herein is to suppress the undesirable signal outside the true depth window that results due to the point spread function from the shape of the spectrum and to further reduce the speckle. It should be noted that the filtering step is not limited to one-dimensional Gaussian filtering and that different filtering methods may be applied and are within the scope of the present disclosure. For example, a two-dimensional filtering may be beneficial for samples that are continuous in the transverse direction. Further, a Hann window may be used for filtering the dataset(s).

Figure 6:
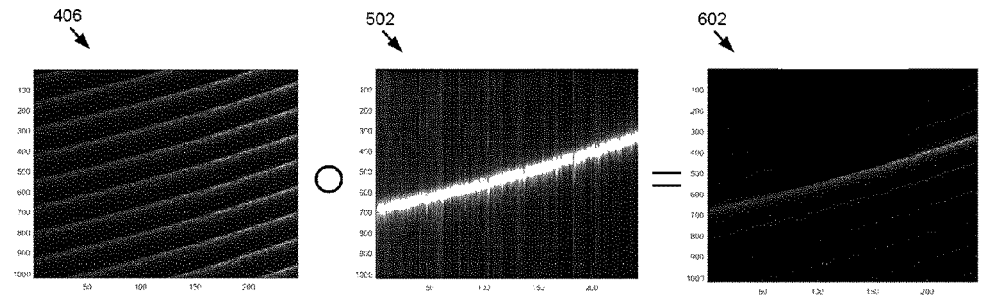
FIG. 6 illustrates an example combination of a broadband sparsely sampled image and the filtered narrowband densely sampled image of FIG. 5 according to one embodiment of the present invention.

Next, in block 207, the broadband and (optionally filtered) narrowband sampled datasets can be combined. For instance, as shown in FIG. 6, the broadband sparsely sampled dataset or image (406) is multiplied by the filtered narrowband densely sampled dataset or image (502). Because the true signal is high in both images, their product reveals the pixels of the true image (602) while suppressing the duplicates and the signals outside the target window. It should be realized that the combining step is not limited to multiplication of the two datasets.

Different calculations involving the processed/unprocessed datasets using different sampling techniques may be used for combination purposes. In some instances, the individual narrowband densely sampled dataset may be sufficient for detecting the true imaging depth window, and the combined dataset could be this individual dataset.

Next, in block 209, a true imaging depth window can be detected from the combined dataset (e.g., image 602) obtained in block 207. Two example approaches may be used for this window detection. One approach compares the corresponding pixels in different imaging depth windows and uses the one with the maximum signal as the true imaging depth window. The other approach computes the center of mass of each A-scan and set the window of a pre-defined depth extent (e.g., the depth extent of the baseband window) around it.

Figure 7A:
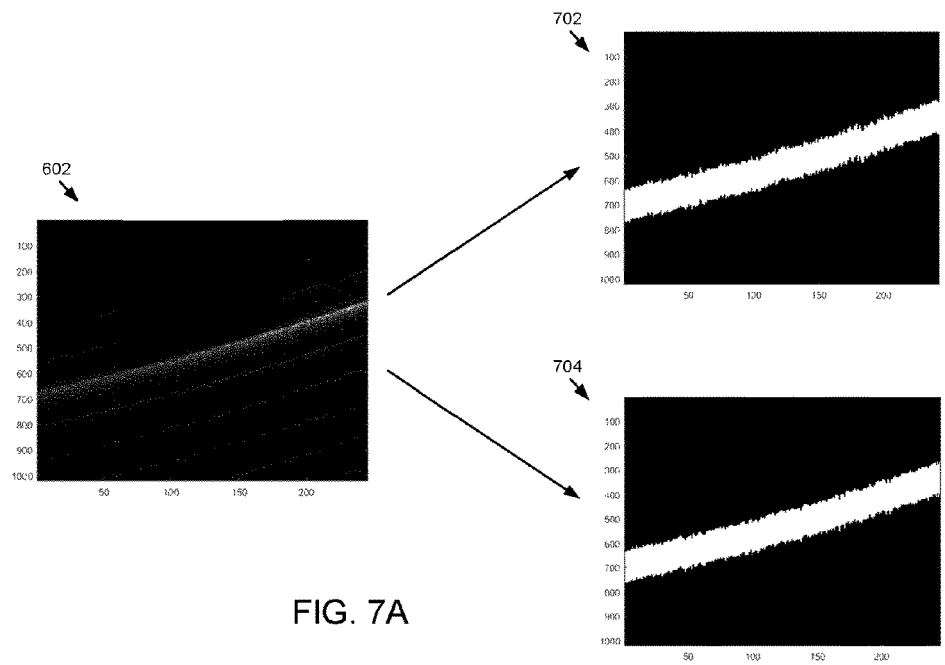
FIG. 7A illustrates examples of detecting a true imaging depth window from the combined result of FIG. 6 using two different detection approaches.
Figure 7B:
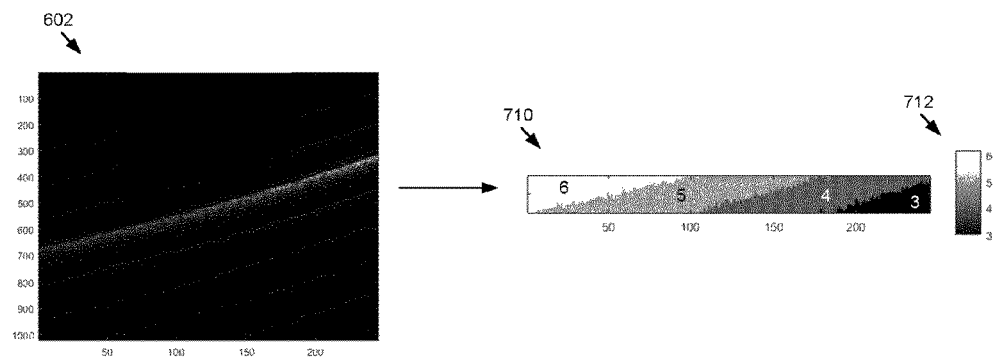
FIGS. 7B and 7C each shows another representation of the detected true imaging depth window from the combined result of FIG. 6 using one of the two detection approaches.
Figure 7C:
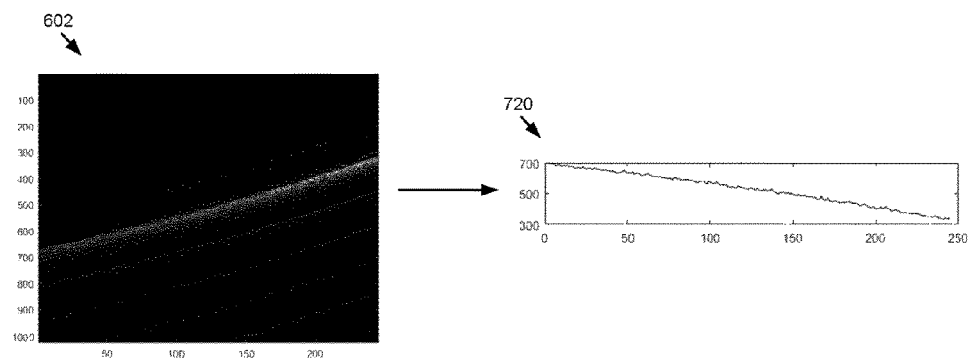

The detected imaging window using either of the two approaches can be represented in a number of ways. In a first exemplary way, the detected window is represented as a binary mask with 1's within the window and 0's elsewhere. For instance, the true imaging depth window detected using the maximum-signal approach can be represented as the binary mask image 702, and the depth window detected using the center-of-mass approach can be represented as the binary mask image 704 (FIG. 7A). In a second exemplary way, the detected window can be represented as a wrapped window 710 (see FIG. 7B) with a depth dimension equal to the baseband image 408 (see FIG. 4B) and the pixel values corresponding to the levels of wrapping (3-6 as shown in scale bar 712). In a third exemplary way, the detected window can be represented as a depth indicator 720 (see FIG. 7C) depicting a characteristic depth location in an image of the sample (e.g., the sample 110) and a predefined depth range around the depth location described by the depth indicator 720.

In block 211, the detected window is used to reconstruct a high-axial-resolution dataset or image over the extended depth range. FIGS. 8A-8D illustrate exemplary ways of producing the high-axial-resolution image. With respect to FIG. 8A, the binary mask representation of the depth window detected using the maximum signal approach 702 is used for image reconstruction. The high-axial-resolution broadband sparse sampling image with duplicates 406 is multiplied by the binary mask image 702 to produce a final image 802. With respect to FIG. 8B, the binary mask representation of the depth window detected using the center-of-mass approach 704 is used for image reconstruction. The high-axial-resolution broadband sparse sampling image with duplicates 406 is multiplied by the binary mask image 704 to produce a final image 804. With respect to FIG. 8C, the wrapped window representation of the depth window 710 (see FIG. 7B) is used to unwrap the baseband image 408 to produce the final image 802. In some instances, a final image (e.g., image 802a) may also be produced by overlaying the baseband image 408 with a transparent version of the wrapped window 710. For visualization of the final image 802a, the transparent wrapped window may be color-coded, or the wrapped window may be used to color-code the baseband image 408. With respect to FIG. 8D, each A-scan in the baseband image 408 is roughly centered in the axial dimension to form a centrally aligned baseband image 408a such that the signals are not wrapped. The centrally aligned baseband image 408a and the depth indicator 720 can be displayed to a user so that the tissue structure and its explicit depth location can be identified. Optionally, the centrally aligned image 408a can be positioned relative to the depth location identified by depth indicator 720 to generate the final image 804.

Figure 9:
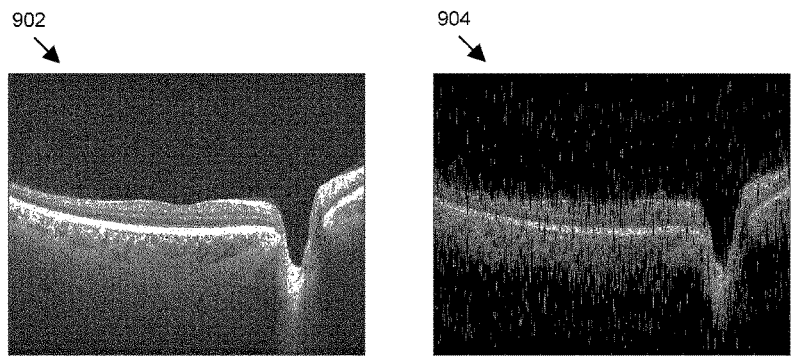
FIG. 9 shows how the center-of-mass method and the maximum-signal method can be combined to yield a better final output image.
Figure 9:
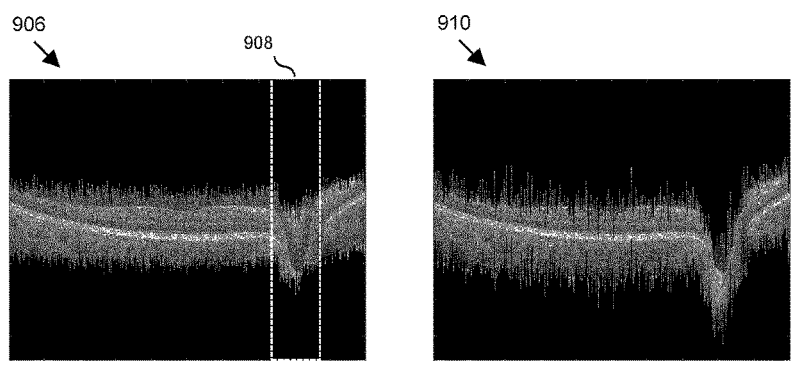

While both window detection methods (i.e., the maximum-signal approach and the center-of-mass approach) successfully detect the true imaging depth window and generate the final images, the maximum-signal approach is pixel-based and likely to be more adaptive to different imaging conditions. The center-of-mass approach is window-based and may be tailored for different applications by tuning the window parameters. The two methods are not mutually exclusive, and can be used in combination. For instance, image 902 in FIG. 9 shows a human eye dataset of lower signal-to-noise ratio. The final image generated by the maximum-signal method (904) includes some noisy signals outside the desired imaging window. The final image generated by the center-of-mass method (906) is affected by the noise such that in some transverse locations (dashed box 908), the detected imaging window is shifted upward and does not reconstruct the image correctly. By applying the center-of-mass method to the image produced by the maximum-signal method 904, the detected imaging depth window better reconstructs the image without noisy signals outside the window (910).

By using the efficient data collection and processing method 200, the data size for acquiring a high-axial-resolution image with an extended depth range of the test eye (discussed in reference to FIG. 4A-C) could be reduced to (128+64−8)/1024~18% as compared to the data size required using the conventional Nyquist sampling method. In a more generalized case, acquiring N and M samples in the broadband sparse sampling and the narrowband dense sampling respectively, the data size is reduced to (N+M−N*M/T)/T, where T is the complete sample number satisfying Nyquist sampling criterion. The sizes of N and M depend on the axial extent of the imaging object and the application needs, as mentioned earlier.

Figure 10A:
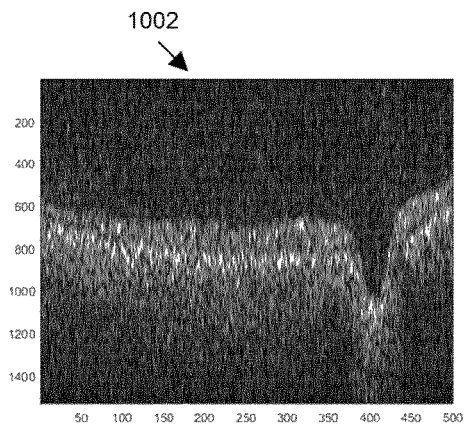
FIG. 10A shows the B-scan and its spectra of the corresponding A-scans of narrowband dense sampling, which is used to determine the numbers of sampling points in the broadband sparse sampling.
Figure 10A:
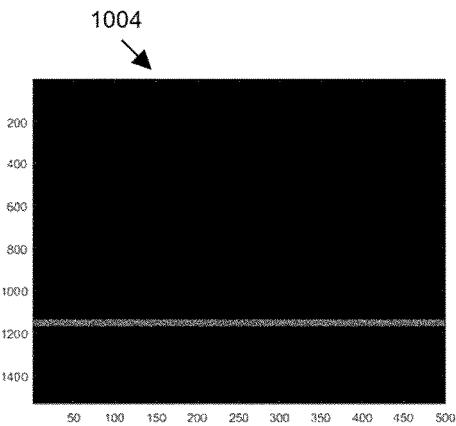
Figure 10B:
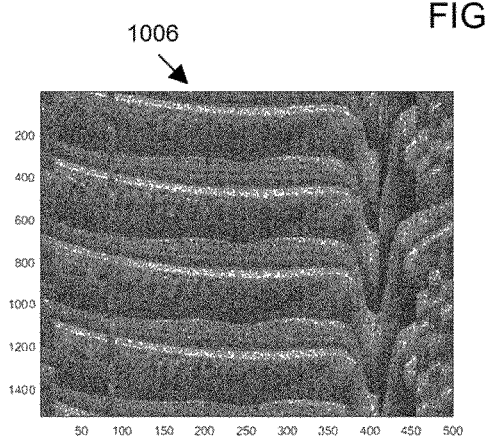
FIG. 10B shows the broadband sparse sampling with varying numbers of sampling points at different transverse locations.
Figure 10B:
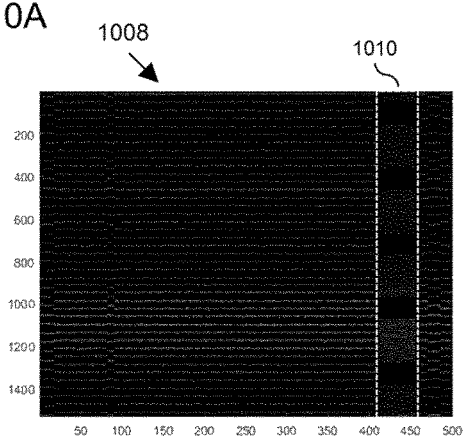
Figure 10C:
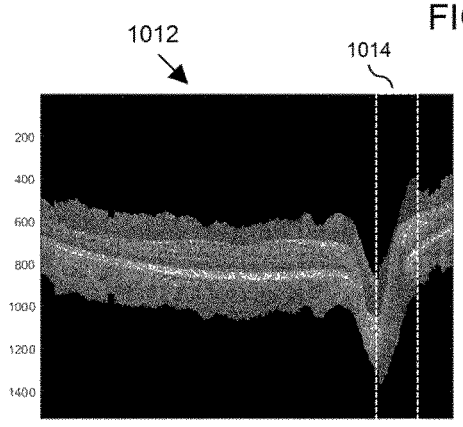
FIG. 10C shows the final output image generated using the center-of-mass approach.

The number of sampling points in the sampling method can be dynamically adjusted when imaging a set of transverse locations on a sample. FIG. 10A-C illustrates an example of using different numbers of broadband sparse sampling points N, when imaging an eye tissue with varying thickness at different transverse locations. A larger N can be used to image locations of thicker tissue, while a smaller N can be used to image locations of thinner tissue. FIG. 10A shows the B-scan (1002) and the interference spectra of corresponding A-scans (1004) of the narrowband dense sampling. For each transverse location, N can be inferred from the depth extent of the corresponding low-axial-resolution A-scan from the narrowband dense sampling. One example approach for inferring the depth extent would be by computing the standard deviation of the signals' axial location. FIG. 10B shows the B-scan (1006) and the interference spectra of corresponding A-scans (1008) of the broadband sparse sampling with varying N. FIG. 10C shows the final output B-scan image generated from the narrowband dense sampling dataset (FIG. 10A) and the broadband sparse sampling dataset with varying N (FIG. 10B), by use of the center-of-mass approach. Note that the depth extent of the imaging window is varied across the B-scan to image tissue of different thickness. For instance, in the dashed box 1014, the depth extent of the imaging window is longer than the rest of A-scans to capture the steep slope of the tissue. The corresponding broadband sparse sampling (1010) has a relatively larger N. A key point here is that the number of sampling points can be adjusted based the measured thickness of the tissue. The number of sampling points can either be varied dynamically across the imaging, or set at a fixed number for the acquisition based on one or more measurements of the thickness of the tissue.

The signal-to-noise-ration (SNR) in the human eye imaging example (FIGS. 4A-C) is reduced to ⅛ of the original as only ⅛ photons are used to generate the image. Therefore, for a fixed integration time per spectral sample, the SNR is reduced by N times. In other words, by using an N-times integration time per spectral sample so that the A-scan time remains, the SNR is the same through efficient sampling. The integration time per spectral samples or the optical power for imaging can also be varied when imaging a set of transverse locations on a sample so that the SNR of the A-scans in a tomogram or a volume is kept the same. Alternatively, one can think of the compressive sensing as increasing the scan depth for a given number of acquisitions. Looked at from this perspective, the signal strength is relatively unchanged as the same number of photons are used to generate the image.

It should be understood that the efficient data collection and processing method in the present invention is not limited to one broadband sparsely sampled dataset and one narrowband densely sampled dataset, and that two or more of each dataset could be used and are within the scope of the present disclosure. The collection of the datasets may be sequential or in parallel. By way of example, two or more broadband sparsely sampled datasets may be collected sequentially without a narrowband densely sampled dataset in between them, the vice versa of which may also be true. In some instances, when collecting data over a set of transverse locations on a sample, the number of locations from which the broadband sparsely sampled datasets are acquired are more than the number of locations from which the narrowband densely sampled datasets are acquired or vice versa. For example, when collecting data over a sample that is structurally continuous and smooth in the transverse direction, the explicit depth ranging of multiple A-scans of the broadband sparsely sampled datasets could be determined by a single A-scan of the narrowband densely sampled dataset.

It should be recognized that the spectral sampling parameters in the present invention may be varied. A general case uses more than one broadband sparsely sampled and narrowband densely sampled datasets, each of which possesses a certain central wavelength, a bandwidth, a spectral resolution, and a linear or nonlinear spectral sampling interval that may or may not be the same. For instance, the central wavelengths of each dataset (i.e., at least one broadband sparsely sampled dataset and at least one narrowband densely sampled dataset) could be arbitrary within the spectra of the light sources. The sampling bandwidths could be varied to meet the desired axial resolution. Also, the spectral sampling interval may or may not be fixed, and a non-linear interval could potentially be beneficial. The spectral resolution of each dataset may or may not be the same, depending on the sensitivity roll-offs needed to image the sample. The spectral resolution of each dataset may or may not be smaller than the spectral sampling interval. In one embodiment, the spectral resolution of the narrowband densely sampled dataset can be larger than the spectral sampling interval, as long as the interference signal of the entire sample can be detected by the system given the sensitivity roll-off determined by the spectral resolution. It should be recognized that the proposed efficient data collection and processing method discussed herein could be tailored for different applications including for example, wide-field retinal imaging, biometry, face/body scan, 3D scanner/imager, and other biomedical and industrial uses.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method of collecting and processing OCT data of a sample using an optical coherence tomography (OCT) system, said method comprising:
    collecting a first dataset at a transverse location of the sample, said first dataset comprising spectra of a bandwidth ($\Delta k_1$) sampled at a spectral sampling interval ($dk_1$);
    collecting a second dataset at said a transverse location of the sample, said second dataset comprising spectra of a bandwidth ($\Delta k_2$) sampled at a spectral sampling interval ($dk_2$), wherein $\Delta k_2$ is less than $\Delta k_1$ and $dk_2$ is less than $dk_1$;
    processing the first and the second datasets together to generate at least one A-scan, wherein the processed A-scan has an axial resolution greater than the axial resolution corresponding to $\Delta k_2$ and a depth range greater than the depth range provided by $dk_1$; and
    storing or displaying the results of said processing or a further analysis thereof.

2. The method as recited in claim 1, wherein the processed A-scan has an axial resolution corresponding to the bandwidth $\Delta k_1$, and wherein data from the second dataset is used to determine the axial location of the sample from said at least one A-scan over a range greater than that given by the sampling interval $dk_1$.

3. The method as recited in claim 1, wherein the first dataset is collected before the second dataset.

4. The method as recited in claim 1, wherein the first and/or second datasets are complex-valued datasets.

5. The method as recited in claim 1, wherein the first dataset further comprises a spectral resolution, $\delta k_1$, that is less than the spectral sampling interval, $dk_1$, ($\delta k_1 < dk_1$).

6. The method as recited in claim 1, wherein processing the first and the second datasets comprises:
    combining the first and the second datasets;
    detecting a true imaging depth window from the combined or individual datasets; and
    using the detected true imaging depth window to generate the at least one A-scan.

7. The method as recited in claim 1, wherein said processing is performed in one or more of a spatial domain and spectral domain.

8. The method as recited in claim 6, further comprising:
    prior to said combining, filtering one or more of the first dataset and the second dataset.

9. The method as recited in claim 6, wherein said combining involves multiplying the first dataset by the second dataset.

10. The method as recited in claim 6, wherein said true imaging depth window detection includes using a maximum-signal approach that comprises comparing corresponding pixels in different imaging windows and detecting an imaging window with the maximum signal as the true imaging depth window.

11. The method as recited in claim 6, wherein said true imaging depth window detection includes using a center-of-mass approach that comprises computing a center of mass of each A-scan and setting an imaging window of a predefined depth extent around it.

12. The method as recited in claim 1, wherein the number of spectral samples of the first dataset varies at different transverse locations on a sample.

13. The method as recited in claim 12, wherein the integration time of each spectral sample of the first dataset varies at different transverse locations on a sample.

14. The method as recited in claim 12, wherein the optical power used to acquire the first dataset varies at different transverse locations on a sample.

15. The method as recited in claim 1, wherein the OCT system comprises one of a swept-source OCT (SS-OCT) system, a spectral-domain OCT (SD-OCT) system, and a combination of SS-OCT and SD-OCT systems.

16. The method as recited in claim 1, wherein the processing step generates a plurality of A-scans.

17. An optical coherence tomography (OCT) system for collecting and processing OCT data of a sample, said system comprising:
    a light source for generating a light beam;
    a beam divider for separating the light beam into a sample arm and a reference arm, said sample arm containing the sample to be imaged;
    optics for scanning the beam in the sample arm over a set of transverse locations on the sample;
    a detector for measuring light returned from both the sample arm and the reference arm and generating signals in response thereto and;
    a processor for processing the signals and generating data based on the processed signals,
    said OCT system capable of scanning the sample in a first mode and a second mode, wherein:
        the sample is scanned in the first mode to obtain a first dataset, wherein the first dataset comprises spectra of a bandwidth ($\Delta k_1$) sampled at a spectral sampling interval ($dk_1$),
        the sample is scanned in the second mode to obtain a second dataset, wherein the second OCT dataset comprises spectra of a bandwidth ($\Delta k_2$) sampled at a spectral sampling interval ($dk_2$), wherein $\Delta k_2$ is less than $\Delta k_1$ and $dk_2$ is less than $dk_1$, and
        said processor processes the first dataset and the second dataset to generate at least one A-scan, said A-scan having an axial resolution greater than the axial resolution provided by $\Delta k_2$ and a depth range greater than the depth range provided by $dk_1$.

18. The OCT system as recited in claim 17, wherein the processed A-scan has an axial resolution corresponding to the bandwidth $\Delta k_1$, and wherein data from the second dataset is used to determine the axial location of the sample from said at least one A-scan over a range greater than that given by the sampling interval $dk_1$.

19. The OCT system as recited in claim 17, wherein the detector is a quadrature detection apparatus for acquiring complex-valued interference signals.

20. The OCT system as recited in claim 17, wherein the processor performs the following steps to generate the at least one A-scan: combining the first and the second datasets; detecting a true imaging depth window from the combined or individual datasets; and using the detected true imaging depth window to generate the at least one A-scan.

21. The OCT system as recited in claim 17, wherein the FD-OCT system comprises one of a swept-source OCT (SS-OCT) system, a spectral-domain OCT (SD-OCT) system, and a combination of SS-OCT and SD-OCT systems.

* * * * *